United States Patent

Borer et al.

[11] Patent Number: 4,464,300
[45] Date of Patent: Aug. 7, 1984

[54] TRIAZOLO BENZAZEPINES

[75] Inventors: René Borer; Max Gerecke; Emilio Kyburz, all of Reinach, Switzerland

[73] Assignee: Hoffmann-La Roche Inc., Nutley, N.J.

[21] Appl. No.: 398,481

[22] Filed: Jul. 15, 1982

[30] Foreign Application Priority Data

Aug. 12, 1981 [CH] Switzerland .................. 5201/82

[51] Int. Cl.³ .................. A61K 31/55; C07D 487/04
[52] U.S. Cl. .................. 260/245.5; 204/158 R; 204/158 HA; 260/243.3; 260/244.4; 260/239 BB; 260/239.3 B; 424/248.4; 424/250; 424/263; 424/269; 546/328; 546/333; 562/426; 562/496; 564/221; 564/265; 564/327; 568/328
[58] Field of Search ............ 260/245.5, 243.3, 244.4

[56] References Cited

U.S. PATENT DOCUMENTS 3,850,942 11/1974 Hester et al. .................. 260/245.5
3,853,882 12/1974 Szmuszkovicz .................. 260/245.5
4,275,066 6/1981 Guzzi et al. .................. 260/245.5
4,297,280 10/1981 Hirai et al. .................. 260/245.5

FOREIGN PATENT DOCUMENTS 759099 4/1971 Belgium .................. 260/245.5
72029 2/1983 European Pat. Off. ......... 260/245.5
100095 9/1976 Japan .................. 260/245.5

Primary Examiner—Alton D. Rollins
Attorney, Agent, or Firm—Jon S. Saxe; Bernard S. Leon; Frank P. Hoffman

[57] ABSTRACT

There are presented benzazepines of the formula

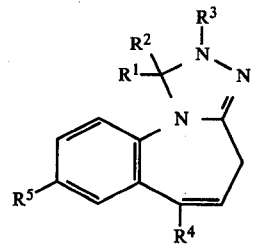

wherein either $R^1$ is hydrogen, lower alkyl, 4-pyridyl or the group $-(CH_2)_n-NR^6R^7$ and $R^2$ and $R^3$ together are an additional bond or $R^1$ and $R^2$ together are the oxo group and $R^3$ is hydrogen or lower alkyl, $R^4$ is phenyl, o-halophenyl or 2-pyridyl, $R^5$ is halogen or nitro and either $R^6$ is hydrogen or lower alkyl and $R^7$ is hydrogen, lower alkyl, lower alkenyl or lower alkynyl or $R^6$ and $R^7$ together with the nitrogen atom are 4-(lower alkyl)-1-piperazinyl or 4-morpholinyl and n is the number 0 or 1, and their pharmaceutically acceptable acid additions salts.

The compounds possess interesting psychotropic properties, i.e., pronounced anxiolytic properties have been established in the case of certain representative members of this class of substance.

9 Claims, No Drawings

TRIAZOLO BENZAZEPINES

DESCRIPTION OF THE INVENTION

The present invention is concerned with benzazepines. More particularly, the invention is concerned with triazolobenzazepines of the formula

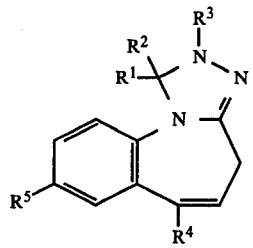

wherein either $R^1$ is hydrogen, lower alkyl, 4-pyridyl or the group $-(CH_2)_n-NR^6R^7$ and $R^2$ and $R^3$ together are an additional bond or $R^1$ and $R^2$ together are the oxo group and $R^3$ is hydrogen or lower alkyl, $R^4$ is phenyl, o-halophenyl or 2-pyridyl, $R^5$ is halogen or nitro and either $R^6$ is hydrogen or lower alkyl and $R^7$ is hydrogen, lower alkyl, lower alkenyl or lower alkynyl or $R^6$ and $R^7$ together with the nitrogen atom are 4-(lower alkyl)-1-piperazinyl or 4-morpholinyl and n is the number 0 or 1, and the pharmaceutically acceptable acid addition salts thereof.

These compounds are novel and possess interesting pharmacological properties.

Objects of the present invention are benzazepines of formula I above and their pharmaceutically acceptable acid addition salts per se and as pharmaceutically active substances, the manufacture of these compounds and intermediates for the manufacture of these compounds, medicaments containing one or more compounds of formula I or pharmaceutically acceptable acid addition salts thereof and the manufacture of such medicaments, as well as the use of benzazepines of formula I and of pharmaceutically acceptable acid addition salts thereof in the control or prevention of illnesses.

The term "lower" in combinations such as "lower alkyl", "lower alkenyl", "lower alkynyl" and the like signifies that the corresponding groups contain at most 7, preferably at most 4, carbon atoms. The term "lower alkyl" denotes straight-chain or branched-chain saturated hydrocarbon groups such as methyl, ethyl, n-propyl, isopropyl, isobutyl, n-butyl, t-butyl and the like. The term "lower alkenyl" embraces groups such as allyl, butenyl, isobutenyl and the like. The term "lower alkynyl" embraces groups such as propargyl and the like. The term "halogen" signifies fluorine, chlorine, bromine or iodine.

In a preferred embodiment, the present invention embraces compounds of formula I above in which either $R^1$ is hydrogen, methyl or aminomethyl and $R^2$ and $R^3$ together are an additional bond or $R^1$ and $R^2$ together are the oxo group and $R^3$ is hydrogen. $R^4$ preferably is o-chlorophenyl or o-fluorophenyl. $R^5$ preferably is chlorine.

Especially preferred compounds in the scope of the present invention are:

8-Chloro-6-(2-fluorophenyl)-2,4-dihydro-1H-s-triazolo[4,3-a][1]benzazepin-2-one,
1-(aminomethyl)-8-chloro-6-(2-fluorophenyl)-4H-s-triazolo[4,3-a][1]benzazepine and
8-chloro-6-(2-fluorophenyl)-1-methyl-4H-s-triazolo[4,3-a][1]benzazepine.

The novel compounds of formula I above and their pharmaceutically acceptable acid addition salts can be manufactured in accordance with the invention by (a) cyclizing a compound of the formula

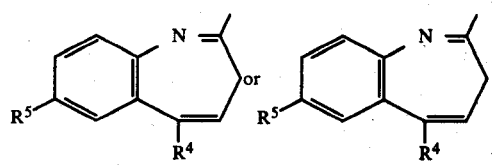

wherein $R^1$, $R^3$, $R^4$ and $R^5$ are as above and X is a leaving group, or (b) hydrolyzing a compound of the formula

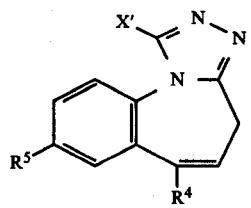

wherein $R^4$ and $R^5$ are as above and X' is a leaving group, or (c) alkylating a compound of the formula

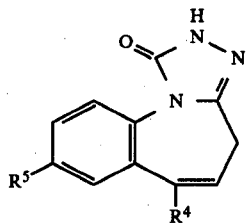

wherein $R^4$ and $R^5$ are as above with an agent yielding a lower alkyl group, or (d) reacting a compound of the formula

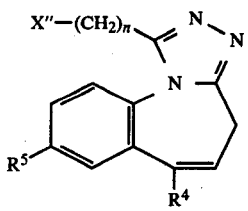

wherein $R^4$, $R^5$ and n are as above and X'' is a leaving group
with an amine of the formula $$R^6R^7NH \qquad VI$$

wherein $R^6$ and $R^7$ are as above or (e) cleaving off the protecting group from a compound of the formula

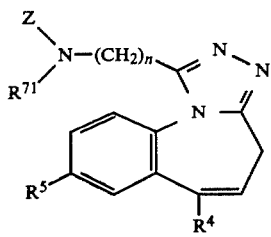

VII wherein $R^4$, $R^5$ and n are as above and either Z is a protecting group and $R^{71}$ is hydrogen, lower alkyl, lower alkenyl or lower alkynyl or Z and $R^{71}$ together are a protecting group or (f) reducing a compound of the formula

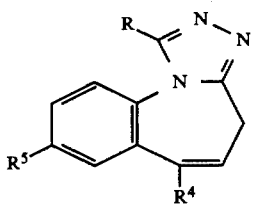

VIII wherein R is azido, azidomethyl, cyano or the group $R^6R^7N$—CO— and $R^4$, $R^5$, $R^6$ and $R^7$ are as above or (g) dehydrogenating a compound of the formula

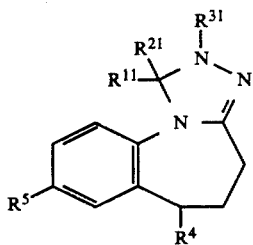

IX wherein either $R^{11}$ is hydrogen or lower alkyl and $R^{21}$ and $R^{31}$ together are an additional bond or $R^{11}$ and $R^{21}$ together are the oxo group and $R^{31}$ is hydrogen or lower alkyl and $R^4$ and $R^5$ are as above or (h) replacing the amino group in a compound of the formula

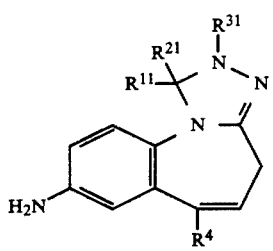

X wherein $R^{11}$, $R^{21}$, $R^{31}$ and $R^4$ are as above by a halogen atom or the nitro group, or (i) reacting a compound of the formula

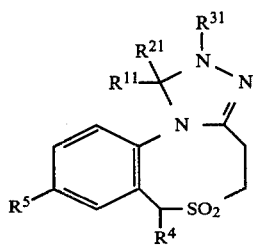

XI wherein $R^{11}$, $R^{21}$, $R^{31}$, $R^4$ and $R^5$ are as above in the presence of a strong base with carbon tetrachloride and t-butanol, and (j) if desired, converting a compound of formula I obtained into a pharmaceutically acceptable acid addition salt.

In accordance with process variant (a), compounds of formula I can be manufactured by cyclizing a compound of formula II or III. This ring-closure reaction is carried out quite readily and can be accomplished, if necessary, by leaving to stand for a long time and/or by the application of heat. The cyclization is conveniently carried out in an inert organic solvent at temperatures of about room temperature to about 180° C., preferably at the boiling point of the mixture. Suitable solvents for the present process aspect are, for example, hydrocarbons such as benzene, toluene, xylene and the like, halogenated hydrocarbons such as chloroform, methylene chloride, chlorobenzene and the like, ethers such as tetrahydrofuran, dioxan, diethylene glycol dimethyl ether, diethylene glycol diethyl ether and the like, alcohols such as methanol, ethanol, n-propanol, isopropanol, n-butanol, isobutanol, cyclohexanol and the like, hexamethylphosphoric acid triamide, dimethylformamide, dimethyl sulphoxide, acetic acid and the like. The compounds of formula II or III need not necessarily be used in the isolated state, and in many cases this is not even possible. As a rule, it has been found to be convenient to cyclize the compounds of formula II or III directly or to leave the compounds of formula II or III to cyclize without isolation from the mixture in which they have been prepared.

The leaving group denoted by X in a compound of formula III is preferably a chlorine atom or a 1-imidazolyl group.

In accordance with process variant (b), compounds of formula I in which $R^1$ and $R^2$ together are the oxo group and $R^3$ is hydrogen can be manufactured by hydrolyzing a compound of formula IV. The leaving group denoted by X' in a compound of formula IV is preferably a bromine atom or an alkoxy, acyloxy or alkylthio group. The hydrolysis is carried out according to methods which are known per se and familiar to any person skilled in the art; depending on the leaving group used the hydrolysis can be carried out under acidic or basic conditions. Compounds of formula IV in which X' is a bromine atom or an alkoxy, alkylthio or mercapto group can be hydrolyzed under acidic conditions, for example using concentrated phosphoric acid, hydrobromic acid, hydrochloric acid and the like. Compounds of formula IV in which X' is an acyloxy group are conveniently hydrolyzed under basic conditions, for example using aqueous potassium hydroxide, aqueous sodium hydroxide, aqueous potassium carbonate and the like. If necessary, the hydrolysis can be carried out in the presence of a solubilizer, suitable solubilizers being, for example, tetrahydrofuran, dioxan, dimethylformamide, alcohols and the like. Compounds of formula IV in which X' is a sulphur-containing leaving group can, however, also be hydrolyzed in the presence of mercury salts in an aqueous system. The hydrolysis is conveniently carried out in a temperature range of about room temperature to the boiling point of the mixture.

In accordance with process variant (c), compounds of formula I in which $R^1$ and $R^2$ together are the oxo group and $R^3$ is lower alkyl can be manufactured by alkylating a compound of formula Ia with an agent yielding a lower alkyl group. Any suitable alkylating agent can be used in the present process aspect. Conveniently, there are used halides such as, for example, methyl iodide, ethyl iodide, isopropyl bromide, n-propyl bromide and the like, dialkyl sulphates such as, for example, dimethyl sulphate and diethyl sulphate, or the like and the alkylation is carried out in an inert organic solvent, for example in an ether (e.g. tetrahydrofuran, dioxan and diethyl ether) or in acetone, N,N-dimethylformamide or the like, in the presence of an acid-binding agent such as, for example, potassium and sodium carbonate, conveniently at room temperature. In an especially preferred embodiment, there is used as the alkylating agent a diazoalkane such as diazomethane or diazoethane in an inert organic solvent. Suitable solvents are, for example, ethers such as diethyl ether and t-butyl methyl ether or mixtures thereof with alcohols such as methanol and ethanol, methylene chloride, chloroform or the like. In this case, the alkylation is preferably carried out at temperatures below room temperature, conveniently at about 0° C.

In accordance with process variant (d), compounds of formula I in which $R^1$ is the group $-(CH_2)_n-NR^6R^7$ and $R^2$ and $R^3$ together are an additional bond can be manufactured by reacting a compound of formula V with an amine of formula VI. The leaving group denoted by X'' in a compound of formula V embraces halogen atoms such as chlorine, bromine and iodine, sulphonic acid groups such as methanesulphonyloxy, p-toluenesulphonyloxy, p-bromobenzenesulphonyloxy and benzenesulphonyloxy, and other equivalent leaving groups. This reaction is conveniently carried out in an inert organic solvent in the presence of an acid-binding agent. Suitable solvents for the present process aspect are, for example, ethers such as diethyl ether, t-butyl methyl ether, tetrahydrofuran, ethylene glycol dimethyl ether and the like, alcohols such as ethanol, ethylene glycol and the like, acetone, dimethylformamide, dimethyl sulphoxide or excess amine of formula VI. As acid-binding agents there come into consideration inorganic bases such as potassium and sodium carbonate or the like or organic bases such as triethylamine, quinuclidine, pyridine or the like, or excess amine of general formula VI. The reaction temperature can vary in a range of about 0° C. to the boiling point of the reaction mixture and is, of course, dependent on the reactivity of the leaving group denoted by X''.

In accordance with process varient (e), compounds of formula I in which $R^1$ is the group $-(CH_2)-NR^6R^7$, $R^2$ and $R^3$ together are an additional bond and $R^6$ is hydrogen can be manufactured by cleaving off the protecting group from a compound of formula VII. Especially suitable protecting groups for the purpose of the present process aspect are acyl groups, preferably readily cleavable alkoxycarbonyl or aralkoxycarbonyl groups, especially the t-butoxycarbonyl group, the benzyloxycarbonyl group etc, as well as readily cleavable aralkyl groups such as the benzyl group.

The removal of the protecting group from a compound of formula VII is carried out according to methods known per se, whereby, of course, the nature of the protecting group to be removed must be taken into consideration when choosing the method to be used. Likewise, it will, of course, be appreciated that there can be used only those methods which selectively remove the protecting group without affecting other structural elements present in the molecule.

The groups mentioned above as examples of protecting groups can be cleaved off hydrogenolytically and/or hydrolytically depending on their nature. Thus, for example, the benzyloxycarbonyl group and the t-butoxycarbonyl group can be cleaved off under selective acidic conditions, for example by treatment with a mixture of hydrogen bromide and glacial acetic acid or by treatment with boron trifluororide or boron tribromide in an inert organic solvent such as methylene chloride. The t-butoxycarbonyl group can also be cleaved off by treatment with hydrogen chloride in an inert organic solvent such as dioxan, tetrahydrofuran or the like, or by treatment with trifluoroacetic acid. The benzyl group can be removed by catalytic hydrogenation, for example over palladium/carbon. The acetyl group can be cleaved off under mild alkaline conditions, for example with a solution of a sodium alcoholate in the corresponding alcohol (such as methanolic sodium methylate).

If Z and $R^{71}$ in a compound of formula VII together are a single protecting group, then there primarily come into consideration cyclic imides, for example phthalimides. Such a protecting group can be removed readily, for example with hydrazine.

In accordance with process variant (f), compounds of formula I in which $R^1$ is amino or the group $-CH_2-NR^6R^7$ and $R^2$ and $R^3$ together are an additional bond can be manufactured by reducing a compound of formula VIII. Examples of suitable reducing agents for the present process aspect are, depending on the nature of the group to be reduced, elementary hydrogen in the presence of a catalyst such as palladium/carbon, Raney-nickel, platinum oxide and the like, complex metal hydrides such as lithium aluminium hydride, and the like. The conditions required for this reduction can be ascertained readily by any person skilled in the art.

In accordance with process variant (g), compounds of formula I in which either $R^1$ is hydrogen or lower alkyl and $R^2$ and $R^3$ together are an additional bond or $R^1$ and $R^2$ together are the oxo group and $R^3$ is hydrogen or lower alkyl can be manufactured by dehydrogenating a compound of formula IX. This dehydrogenation can be carried out, for example, with an oxidizing agent such as 2,3-dichloro-5,6-dicyanobenzoquinone in an inert organic solvent such as benzene, toluene and the like. In this case, the oxidation is carried out in a temperature range of about room temperature to the boiling point of the solvent.

The above dehydrogenation can, however, also be carried out by treating a compound of formula IX in an inert organic solvent with a brominating agent. Suitable brominating agents are, for example, N-bromosuccinimide, N-bromoacetamide and elementary bromine. When elementary bromine is used, the treatment is conveniently carried out in the presence of light. As solvents there come into consideration in this case primarily halogenated hydrocarbons such as, for example, methylene chloride, 1,2-dichloroethane, chloroform, carbon tetrachloride and the like, or other inert organic solvents such as, for example, acetonitrile, ethers etc. The treatment is preferably carried out at temperatures of about 0° C. up to the boiling point of the chosen solvent.

In accordance with process variant (h), compounds of formula I in which either $R^1$ is hydrogen or lower alkyl and $R^2$ and $R^3$ together are an additional bond or $R^1$ and $R^2$ together are the oxo group and $R^3$ is hydrogen or lower alkyl can be manufactured by replacing the amino group in a compound of formula X by a halogen atom or the nitro group. In this case, the amino compound of formula X is conveniently converted into a corresponding diazonium salt and this is reacted, optionally without previous isolation, with a nitrite such as sodium nitrite, or with a halide (e.g. with a chloride or bromide) in the presence of a copper (I) salt. The presence of a copper (I) salt is not necessary for the manufacture of the corresponding iodides. Corresponding fluorides are conveniently manufactured via the corresponding diazonium tetrafluoroborates, for example by irradiation with UV-light. These reactions are carried out in aqueous solution at temperatures of about $-10°$ C. to about room temperature.

An amino compound of formula X can, however, also be converted into the corresponding nitro compound by oxidation. Suitable oxidizing agents are, for example, peracids such as peracetic acid, trifluoroperacetic acid, m-chloroperbenzoic acid and perbenzoic acid, or the like. As solvents there come into consideration, depending on the oxidizing agent used, carboxylic acids such as acetic acid etc, halogenated hydrocarbons such as methylene chloride, chloroform, 1,2-dichloroethane etc, or the like. As a rule, this oxidation is carried out at temperatures of about 0° C. to about room temperature.

In accordance with process variant (i), compounds of formula I in which either $R^1$ is hydrogen or methyl and $R^2$ and $R^3$ together are an additional bond or $R^1$ and $R^2$ together are the oxo group and $R^3$ is hydrogen or lower alkyl can be manufactured by reacting a compound of general formula XI in the presence of a strong base with carbon tetrachloride and t-butanol. Suitable strong bases are, for example, alkali metal hydroxides such as sodium and potassium hydroxide and alkali metal alcoholates such as potassium t-butanolate. In a preferred embodiment, the reaction is carried out in the presence of a small amount of water. The reaction temperature conveniently lies in a range of about room temperature to about 80° C.

In accordance with process variant (j), compounds of formula I can be converted into pharmaceutically acceptable acid addition salts. The manufacture of such pharmaceutically acceptable acid addition salts is carried out according to generally usual methods. There come into consideration not only salts with inorganic acids but also salts with organic acids; for example, hydrochlorides, hydrobromides, sulphates, methanesulphonates, p-toluenesulphonates, oxalates, maleates, fumarates and the like.

The compounds of formulae II and III which are used as starting materials can be prepared starting from compounds of the formula

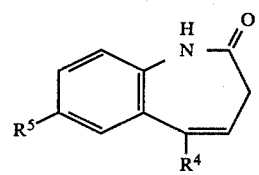

XII wherein $R^4$ and $R^5$ are as above in accordance with Formula Scheme I hereinafter in which $R^1$, $R^3$, $R^4$, $R^5$ and X are as above and X''' is a leaving group:

Formula Scheme I

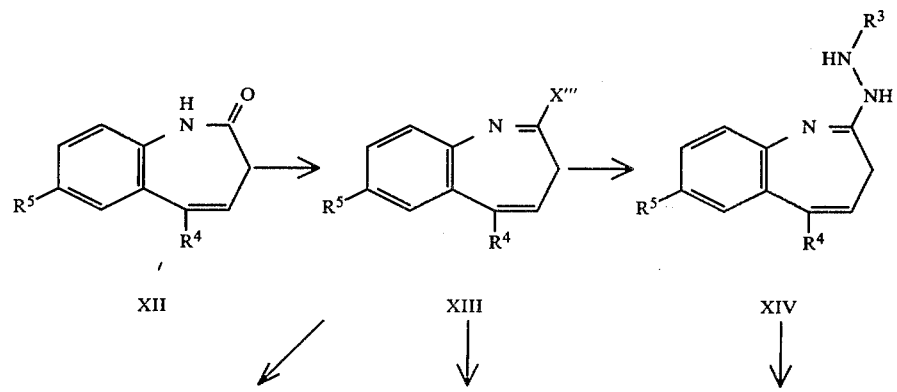

-continued
Formula Scheme I

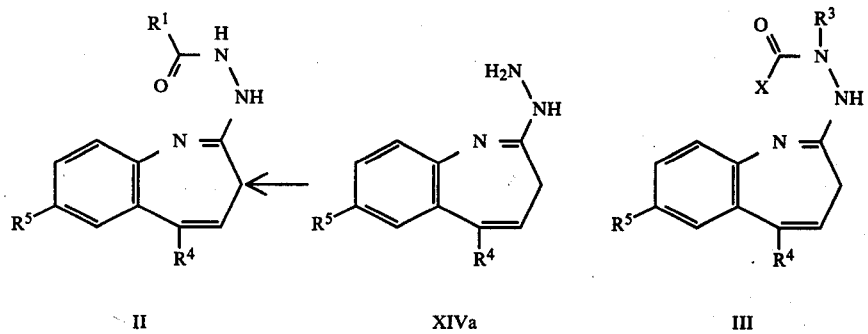

II  XIVa  III

The leaving group denoted by X''' in formula XIII is, for example, a readily cleavable phosphinyl group, for example a group of the formula

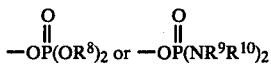

wherein $R^8$ is lower alkyl and $R^9$ and $R^{10}$ each are lower alkyl, allyl, phenyl or substituted phenyl or $R^9$ and $R^{10}$ together with the nitrogen atom are an unsubstituted or substituted 3- to 8-membered heterocyclic ring (e.g. morpholine), a halogen atom, an alkylthio group, an aralkylthio group, a N-nitrosoalkylamino group, an alkoxy group, a mercapto group and the like (when X''' is a mercapto group, then the corresponding compound of formula XIII is the iminothiol form of the corresponding thiolactam). The compounds of formula XIII can be prepared according to methods known per se from compounds of formula XII; see, for example, Belgian Patent Specifications Nos. 802 233, 833 249 and 865 653, American Patent Specification No. 3 681 341 and J. Org. Chemistry 29, 231 (1964).

By reacting a compound of formula XIII with a hydrazine of the formula $R^3NH-NH_2$, wherein $R^3$ is as above in an inert organic solvent there is obtained a compound of formula XIV. Suitable solvents are, for example, ethers such as tetrahydrofuran, dioxan, t-butyl methyl ether, ethylene glycol dimethyl ether and the like, alcohols such as methanol, ethanol and the like, acetone, dimethylformamide etc. In this case, the reaction is carried out in a temperature range of about 0° C. up to the boiling point of the reaction mixture, but preferably at room temperature.

By reacting a compound of formula XIV with a reactive derivative of carbonic acid there is obtained a compound of formula III. Suitable reactive derivatives of carbonic acid are, for example, phosgene, N,N'-carbonyldiimidazole and the like. The reaction is conveniently carried out in an inert organic solvent, for example an ether such as tetrahydrofuran, dioxan, t-butyl methyl ether, ethylene glycol dimethyl ether and the like, a hydrocarbon such as benzene, toluene, xylene and the like, dimethylformamide, acetonitrile etc. If phosgene is used as the reactive carbonic acid derivative, then the reaction is advantageously carried out in the presence of an acid-binding agent. Especially preferred acid-binding agents are, for example, tertiary amines such as pyridine, triethylamine, quinuclidine and the like.

The compounds of formula II can be prepared by reacting a compound of formula XIVa with a reactive derivative of a carboxylic acid of the formula $R^1COOH$, wherein $R^1$ is as above. Suitable reactive carboxylic acid derivatives are, for example, the corresponding esters, orthoesters, anhydrides, halides etc.

The following solvents are suitable depending on the reactivity of the carboxylic acid derivative used: ethers such as tetrahydrofuran, diethyl ether, dioxan, ethylene glycol dimethyl ether and the like, alcohols such as methanol, ethanol, n-butanol, i-propanol and the like, dimethyl sulphoxide, dimethylformamide, acetonitrile etc. The reaction is conveniently carried out in a temperature range of about 0° C. up to the boiling point of the reaction mixture.

The compounds of formula II can, however, also be prepared by reacting a compound of formula XIII with a compound of the formula $R^1CO-NH-NH_2$, wherein $R^1$ is as above. In this case, the reaction is conveniently carried out in an inert organic solvent, with alcohols such as methanol, ethanol, n-butanol, i-propanol and the like being preferred. The reaction is preferably carried out in a temperature range of about room temperature up to the boiling point of the reaction mixture.

As mentioned above, it is not necessary (and in many cases even not possible) to isolate the compounds of formulae II and III; rather it has been found to be convenient as a rule to cyclize these compounds directly or to leave these compounds to cyclize without isolation from the reaction mixture in which they have been prepared.

The compounds of formula XII belong to a class of substance known per se. They can be prepared, for example, in accordance with Reaction Scheme II hereinafter in which $R^4$ and $R^5$ are as above:

Scheme II

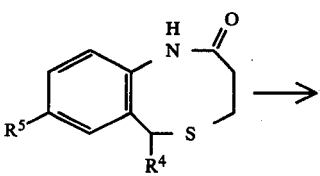

XV

-continued
Scheme II

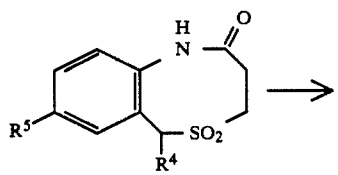

XVI

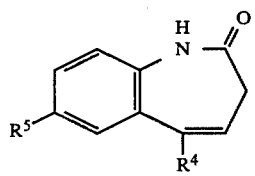

XII

The oxidation of a compound of formula XV to a compound of formula XVI is preferably carried out with an oxidizing agent such as m-chloroperbenzoic acid or the like in an inert organic solvent. Suitable solvents are, for example, halogenated hydrocarbons such as methylene chloride, chloroform, 1,2-dichloroethane or the like. The oxidation is conveniently carried out in a temperature range of about 0° C. up to the boiling point of the mixture, preferably at about room temperature.

The compounds of formula XVI can be converted into compounds of formula XII in analogy to process variant (i).

The compounds of formula IV in which X' is bromine which are used as starting materials can be prepared, for example, by brominating a compound of formula I in which $R^1$ is hydrogen. As the brominating agent there is preferably used elementary bromine in an inert organic solvent, preferably in the presence of an acidbinding agent. Suitable inert organic solvents are, for example, halogenated hydrocarbons such as methylene chloride, chloroform, carbon tetrachloride and the like, alcohols such as methanol, ethanol, i-propanol and the like, ethers such as tetrahydrofuran and dioxan, and the like. A tertiary amine such as pyridine, triethylamine, quinuclidine and the like is preferably used as the acid-binding agent. The bromination is preferably carried out at a temperature in the range of about room temperature to about 70° C.

Compounds of formula IV in which X' is lower alkoxy, lower alkylthio or acyloxy can be prepared by reacting a compound of the formula

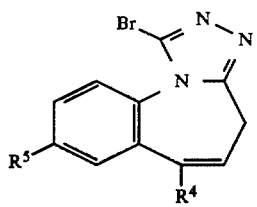

IVa wherein $R^4$ and $R^5$ are as above in the presence of a base with an alcohol or a mercaptan or a carboxylic acid. Suitable bases are, for example, alkali metal hydroxides such as potassium hydroxide jnd sodium hydroxide, alkali metal hydrides such as sodium hydride, alkali metal carbonates such as sodium carbonate and potassim carbonate, tertiary amines such as triethylamine etc. The choice of the suitable solvent and of the suitable reaction temperature presents no difficulties to the person skilled in the art.

The compounds of formulae V and VII which are used as starting materials can be prepared starting from corresponding compounds of formula II in analogy to process variant (a) and to the methods described for the preparation of the corresponding starting materials.

Compounds of formula V in which n is the number 1 can also be prepared starting from compounds of the formula

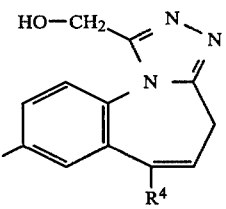

XVII wherein $R^4$ and $R^5$ are as above. The hydroxy group in a compound of formula XVII can be replaced by a leaving group according to methods which are known per se and familiar to any person skilled in the art; for example, by treating such a compound with a halogenating agent such as thionyl chloride, phosphorus oxychloride, phosphorus pentachloride or the like or with a sulphonic acid, for example with methanesulphonic acid chloride, p-toluenesulphonic acid chloride or the like.

The compounds of formula XVII can be prepared starting from corresponding compounds of formula II in analogy to process variant (a) and to the methods described for the preparation of the corresponding starting materials.

Compounds of formula VII in which $R^{71}$ is lower alkyl, lower alkenyl or lower alkynyl can also be prepared by reacting a compound of formula I in which $R^1$ is the group $-(CH_2)_n-NH_2$ with an agent yielding the group Z and appropriately alkylating the resulting compound of the formula

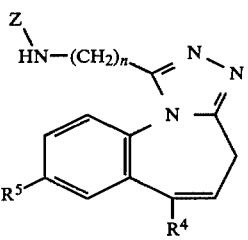

XVIII wherein $R^4$, $R^5$, n and Z are as above.

The compounds of formula VIII in which R is azido, azidomethyl or cyano which are used as starting materials can be prepared by reacting a compound of formula V with an azide such as sodium azide or with a cyanide such as sodium cyanide or potassium cyanide. These reactions can be carried out according to methods which are known per se and familiar to any person skilled in the art.

Compounds of formula VIII in which R is the group $R^6R^7N-CO-$ can be prepared starting from corresponding compounds of formula XII in analogy to process variant (a) and to the methods described for the preparation of the corresponding starting materials.

The compounds of formula IX which are used as starting materials can be prepared in analogy to the manufacture of compounds of formula I from compounds of formula XII, namely starting from compounds of the formula

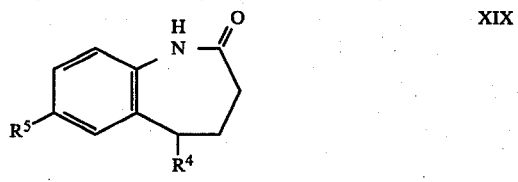

wherein $R^4$ and $R^5$ are as above.

The compounds of formula XIX belong to a class of substance known per se; specific representatives which have not previously been described can be prepared in analogy to the known representatives of this class of substance.

The compounds of formula X which are used as starting materials can be prepared in analogy to the manufacture of compounds of formula I from compounds of formula XII, namely starting from compounds corresponding to formula XII, but in which $R^5$ is a protected amino group. By cleaving off the protecting group denoted by Z' from a thus-obtained compound of the formula

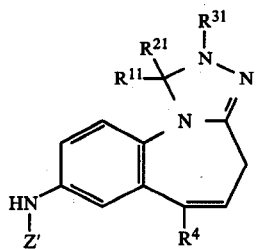

wherein $R^{11}$, $R^{21}$, $R^{31}$ and $R^4$ are as above and Z' is a protecting group, there is obtained a compound of formula X. The protecting group denoted by Z' is preferably an alkoxycarbonyl group (e.g. the ethoxycarbonyl group) which can be cleaved off according to methods known per se. The compounds of formula X can, of course, also be prepared by reducing corresponding nitro compounds.

The compounds of formula XI which are used as starting materials can be prepared starting from compounds of formula XVI in analogy to the manufacture of compounds of formula I from compounds of formula XII.

The compounds of formulae II, III, IV, V, VII, VIII, IX, X and XI are also objects of the present invention.

The compounds of formula I possess interesting pharmacological properties and exhibit only a low toxicity. They display psychotropic activities and can be used as tranquillizers and/or anxiolytics.

Some representative members of the class of compound defined by formula I have been investigated in the tests described below, and it has been shown that in rats and monkeys they display pronounced anxiolytic properties. The test results obtained are compiled in the following Table. Moreover, the Table contains data concerning the acute toxicity of these compounds ($LD_{50}$ in the case of single oral administration to mice).

TABLE

| Compound | Toxicity $LD_{50}$ in mg/kg p.o. | Anti-pentetrazole test, PR 2.0 in mg/kg p.o. | Anti-3-mercaptopropionic test, $ED_{50}$ in mg/kg p.o. | Determination of the motor activity, $ED_{40}$ in mg/kg p.o. | Conflict test in rats, FSD in mg/kg p.o. | Conflict test in monkeys in mg/kg p.o. | |
|---|---|---|---|---|---|---|---|
| | | | | | | MED | HED |
| A | >5000 | 4.1 | 6.0 | >300 | 3 | 1.25 | >80 |
| B | 1000–2000 | 5.8 | 3.7 | >100 | 100 | 1.25 | 10 |
| C | >5000 | 4.0 | 1.9 | 77 | 3 | 10 | >80 |

Compound A: 8-Chloro-6-(2-fluorophenyl)-2,4-dihydro-1H—s-triazolo[4,3-a][1]benzazepin-1-one.
Compound B: 1-(Aminomethyl)-8-chloro-6-(2-fluorophenyl)-4H—s-triazolo[4,3-a][1]benzazepin-1-one.
Compound C: 8-Chloro-6-(2-fluorophenyl)-1-methyl-4H—s-triazolo[4,3-a][1]benzazepin-1-one.

There follows a brief description of the animal tests mentioned in the above Table:

Anti-pentetrazole Test

The compound to be tested is administered orally to groups of 6 female mice (19–21 g) and 30 minutes later there is administered intravenously (0.375 ml/minute) a 0.5 percent solution of pentetrazole in sodium chloride solution. The time from the beginning of the infusion until tonic stretchings of the hind limbs appear is measured and therefrom there is calculated the dosage of penetetrazole administered up to this point in time, which is denoted as the convulsive threshold dosage. The $PR_{2.0}$ is that dosage of the test substance which is required in order that the ratio of the convulsive threshold dosage in treated animals to the convulsive threshold dosage in untreated animals amounts to 2:1.

Anti-3-mercaptopropionic Acid Test

The compound to be tested is administered orally to female mice (19–21 g) and 30 minutes later there are administered i.p. 48.8 mg/kg of 3-mercaptopropionic acid, a dosage which in untreated animals causes after 4 minutes emprosthotonus and tonic stretching of the hind limbs. 12 mice are used per dosage. At least 6 to 8 different dosages are tested. The number of protected test animals per dosage group is determined and the $ED_{50}$ is determined therefrom by means of the Probit method.

Determination of the Motor Activity

Groups each comprising three rats (200 g) are confined in large cages. The test animals can adapt themselves to the new surroundings for 30 minutes; subsequently the test substance is administered to them orally. The spontaneous movements are registered automatically for 2 hours by means of infrared light barriers. The $ED_{40}$ is that dosage which reduces to 40% the mobility of the test animals in comparison to the untreated animals.

Conflict Test in Rats

The test apparatus is a one-key Skinner box with a feed pellet dispenser. For the testing of potential anxiolytics there are generally used 8 fasted rats per substance and dosage. In this case, there are used rats only which respond to the known anxiolytic chlordiazepoxide.

The test substances, which are dissolved or suspended in a mixture of 10 ml of distilled water and 2 drops of Tween 80, are administered to the test animals with the aid of a probang 30 minutes before the 1-hour conflict test. During the experiment, in which each key press for a feed pellet is combined with a foot-shock (conflict), the number of key operations is registered. In this case, each test animal serves as its own control, in that it is pre-treated once with test substance and once with sodium chloride solution.

The first significant anxiolytically-effective dosage (FSD) is determined with the Wilcoxon test (comparison of pairs) by comparing the number of key operations in the main test (feed pellet+foot-shock, after pre-treatment with test substance) directly with the number of key operations in the control test (feed pellet+foot-shock, after pre-treatment with sodium chloride solution).

Conflict Test in Monkeys

A two-key Skinner box with a feed pellet dispenser is used as the test apparatus. 13 fasted, male squirrel monkeys weighing 0.8 to 1 kg are used as the test animals. Upon pressing one of the keys the test animals receive a feed pellet on average every 6 minutes. Upon pressing the other key the test animals receive a feed pellet four times more frequently (i.e. on average every 1.5 minutes), but they are simultaneously punished with an electric foot-shock. The foot-shock causes a reduction in the pressing of the key which gives more frequent feed pellets. Investigations are now carried out as to whether test substances increase significantly the key pressings which are combined with a foot-shock. The smallest (MED) and the highest significant effective dosage (HED) are thereby determined.

The compounds of general formula I and their pharmaceutically acceptable acid addition salts can be used as medicaments, for example in the form of pharmaceutical preparations. The pharmaceutical preparations can be administered orally (e.g. in the form of tablets, coated tablets, dragées, hard and soft gelatine capsules, solutions, emulsions or suspensions). The administration can, however, also be carried out rectally (e.g. in the form of suppositories) or parenterally (e.g. in the form of injection solutions).

For the manufacture of pharmaceutical preparations, the products in accordance with the invention can be processed with pharmaceutical inert, inorganic or organic carriers. Examples of such carriers which can be used for tablets, coated tablets, dragées and hard gelatine capsules are lactose, maize starch or derivatives thereof, talc, stearic acid or its salts and the like. Suitable carriers for soft gelatine capsules are, for example, vegetable oils, waxes, fats, semi-solid and liquid polyols and the like; depending on the nature of the active substance no carriers are, however, generally required in the case of soft gelatine capsules. Suitable carriers for the manufacture of solutions and syrups are, for example, water, polyols, saccharose, invert sugar, glucose and the like. Suitable carriers for injection solutions are, for example, water, alcohols, polyols, glycerine, vegetable oils and the like. Suitable carriers for suppositories are, for example, natural or hardened oils, waxes, fats, semi-liquid or liquid polyols and the like.

The pharmaceutical preparations can also contain preserving agents, solubilizers, stabilizing agents, wetting agents, emulsifying agents, sweetening agents, colouring agents, flavouring agents, salts, for the variation of the osmotic pressure, buffers, coating agents or antioxidants. They can also contain still other therepeutically valuable substances.

As mentioned earlier, medicaments containing a compound of general formula I or a pharmaceutically acceptable acid addition salt thereof are likewise an object of the present invention as is a process for the manufacture of such medicaments which comprises by bringing one or more compounds of general formula I or pharmaceutically acceptable acid addition salts thereof and, if desired, one or more other therapeutically valuable substances into a galenical administration form. A further object of the present invention is, as mentioned at the beginning, the use of compounds of general formula I and their pharmaceutically acceptable acid addition salts in the control or prevention of illnesses, especially in the control or prevention of anxiety states. The dosage can vary within wide limits and is, of course, fitted to the individual requirements in each particular case. In general, in the case of oral administration a daily dosage of about 5 mg to 100 mg should be appropriate.

The following Examples illustrate the present invention in more detail, but are not intended to limit its extent. In the Examples, all temperatures are given in degrees Centigrade.

EXAMPLE 1

(a) A solution of 18.5 g of sodium borohydride in 125 ml of water is added dropwise at 20° to 25° within 20 minutes to a solution of 124.8 g of 2-amino-5-chloro-2'-fluorobenzophenone. The mixture is stirred for a further 16 hours. 250 ml of methanol are then added thereto and the mixture is heated to boiling under reflux for 15 minutes. After evaporation of the organic solvent, the residue is diluted with water, whereupon the mixture is acidified with hydrochloric acid and extracted with ethyl acetate. The ethyl acetate solutions are washed, dried, concentrated to 100 ml in vacuo and subsequently treated with 300 ml of petroleum ether. There is obtained crystalline 2-amino-5-chloro-2'-fluorobenzhydrol of melting point 97°–99°.

(b) 100 g of 2-amino-5-chloro-2'-fluorobenzhydrol, 45.6 g of 3-mercaptopropionic acid and 200 ml of 6N hydrochloric acid are stirred together at 100° for 1.5 hours. After cooling the mixture, the precipitated crystals are filtered off and washed with 6N hydrochloric acid. There is obtained 3-[(2-amino-5-chlorophenyl)(2-fluorophenyl)methylthio]propionic acid hydrochloride of melting point 139°–141°.

(c) 140 g of 3-[(2-amino-5-chlorophenyl)(2-fluorophenyl)methylthio]propionic acid hydrochloride are suspended in 1.4 l of methylene chloride. The suspension is cooled to 0°. At this temperature there are added firstly 104 ml of triethylamine, whereupon within 45 minutes there is added dropwise a solution of 37.1 ml of ethyl chloroformate in 150 ml of methylene chloride. The mixture is then stirred at room temperature for a further 3 hours. The mixture is filtered. The filtrate is washed several times with dilute sulphuric acid and thereafter with water, dried and evaporated. The residue is dissolved in hot toluene and the insoluble constituent is filtered off. The filtrate is concentrated strongly and treated with petroleum ether. 8-Chloro-6-(2-fluorophenyl)-1,3,4,6-tetrahydro-2H-5,1-benzthiazocin-2-one of melting point 222° crystallizes out.

(d) 65 g of 8-chloro-6-(2-fluorophenyl)-1,3,4,6-tetrahydro-2H-5,1-benzthiazocin-2-one are dissolved in 1.95 l of chloroform. While cooling there is added dropwise within 40 minutes a solution of 83.2 g of m-chloroperbenzoic acid in 520 ml of chloroform. The temperature is held between 20° and 22° during the addition. After stirring for a further 90 minutes at room temperature, the solution is filtered over 800 g of aluminium oxide (activity grade I). The substance which is eluted with 2 l of chloroform is recrystallized from methanol/toluene. There is obtained 8-chloro-6-(2-fluorophenyl)-1,3,4,6-tetrahydro-2-oxo-2H-5,1-benzothiazocine 5,5-dioxide of melting point about 265° (decomposition).

(e) 67.0 g of 8-chloro-6-(2-fluorophenyl)-1,3,4,6-tetrahydro-2-oxo-2H-5,1-benzothiazocine 5,5-dioxide are suspended in a mixture of 670 ml of carbon tetrachloride, 670 ml of t-butanol and 31.5 ml of water. The suspension is pre-warmed to 35° C. There are then rapidly added thereto while cooling four 51.5 g portions of potassium t-butylate (the temperature amounts to 45°–50°). The mixture is stirred for a further 35 minutes, the temperature dropping to about 35°. The mixture is poured on to ice, whereupon it is extracted with methylene chloride. The organic phase is evaporated and the residue is triturated with ether. The crystalline product is filtered off. There is obtained 7-chloro-5-(2-fluorophenyl)-1,3-dihydro-2H-1-benzazepin-2-one of melting point 214°–215°.

(f) 20.2 g of 7-chloro-5-(2-fluorophenyl)-1,3-dihydro-2H-1-benzazepin-2-one are dissolved in 110 ml of hexamethylphosphoric acid triamide and treated with 13.8 g of 2,4-bis-(4-methoxyphenyl)-1,3,2,4-dithiadiphosphetane-2,4-disulphide. The mixture is warmed to 100° for 1 hour, again cooled to room temperature and poured into 2.2 l of water. The mixture is extracted three times with ethyl acetate and the organic extracts are washed with water, sodium hydrogen carbonate solution and with saturated sodium chloride solution. The ethyl acetate solutions are evaporated and the residue is chromatographed on 400 g of silica gel. By elution with toluene and toluene/chloroform (19:1) and recrystallization of the resulting material from diisopropyl ether there is obtained 7-chloro-5-(2-fluorophenyl)-1,3-dihydro-2H-1-benzazepine-2-thione of melting point 179°–181°.

(g) 3.9 g of 7-chloro-5-(2-fluorophenyl)-1,3-dihydro-2H-1-benzazepine-2-thione and 4.5 g of acetic acid hydrazide are heated to boiling under reflux in 60 ml of n-butanol for 16 hours. The solution is then evaporated in vacuo and the residue is partitioned between chloroform and water. The chloroform solution is evaporated. The residue is chromatographed on 250 g of silica gel. In order to remove impurities, elution is carried out with a toluene/ethyl acetate mixture, with ethyl acetate and with ethyl acetate/ethanol (99:1 and 95:5). Crude 8-chloro-6-(2-fluorophenyl)-1-methyl-4H-s-triazolo[4,3-a][1]-benzazepine is eluted with ethyl acetate/ethanol (9:1 and 8:2). After recrystallization from isopropanol, the product has a melting point of 224°–226°.

EXAMPLE 2

(a) From 2-amino-2',5-dichlorobenzophenone there is obtained in analogy to Example 1(a) 2-amino-2',5-dichloro-benzhydrol of melting point 97°–100°.

(b) From 2-amino-2',5-dichlorobenzhydrol there is obtained in analogy to Example 1(b) 3-[(2-amino-5-chlorophenyl)(2-chlorophenyl)methylthio]propionic acid hydrochloride of melting point 197° (decomposition).

(c) From 3-[(2-amino-5-chlorophenyl)(2-chlorophenyl)methylthio]propionic acid hydrochloride there is obtained in analogy to Example 1(c) 8-chloro-6-(2-chlorophenyl)-1,3,4,6-tetrahydro-2H-5,1-benzothiazocin-2-one of melting point 258°–260°.

(d) From 8-chloro-6-(2-chlorophenyl)-1,3,4,6-tetrahydro-2H-5,1-benzothiazocin-2-one there is obtained in analogy to Example 1(d) 8-chloro-6-(2-chlorophenyl)-1,3,4,6-tetrahydro-2-oxo-2H-5,1-benzothiazocine 5,5-dioxide of melting point 298°–300°.

(e) From 8-chloro-6-(2-chlorophenyl)-1,3,4,6-tetrahydro-2-oxo-2H-5,1-benzothiazocine 5,5-dioxide there is obtained in analogy to Example 1(e) 7-chloro-5-(2-chlorophenyl)-1,3-dihydro-2H-1-benzazepin-2-one of melting point 194°–198°.

(f) From 7-chloro-5-(2-chlorophenyl)-1,3-dihydro-2H-1-benzazepin-2-one there is obtained in analogy to Example 1(f) 7-chloro-5-(2-chlorophenyl)-1,3-dihydro-2H-1-benzazapine-2-thione of melting point 171°.

(g) From 7-chloro-5-(2-chlorophenyl)-1,3-dihydro-2H-1-benzazepine-2-thione there is obtained in analogy to Example 1(g) 8-chloro-6-(2-chlorophenyl)-1-methyl-4H-s-triazolo[4,3-a][1]benzazepine of melting point 253°–254°.

EXAMPLE 3

(a) From 2-(2-amino-5-bromobenzoyl)pyridine there is obtained in analogy to Example 1(a) (2-amino-5-bromophenyl)(2-pyridyl)methanol of melting point 100°–104°.

(b) From (2-amino-5-bromophenyl)(2-pyridyl)methanol there is obtained in analogy to Example 1(b) 3-[(2-amino-5-bromophenyl)(2-pyridyl)methylthio]propionic acid hydrochloride of melting point 130°–132°.

(c) From 3-[(2-amino-5-bromophenyl)(2-pyridyl)methylthio]propionic acid hydrochloride there is obtained in analogy to Example 1(c) 8-bromo-1,3,4,6-tetrahydro-6-(2-pyridyl)-2H-5,1-benzothiazocin-2-one of melting point 190°191°.

(d) From 8-bromo-1,3,4,6-tetrahydro-6-(2-pyridyl)-2H-5,1-benzothiazocin-2-one there is obtained in analogy to Example 1(d) 8-bromo-1,3,4,6-tetrahydro-2-oxo-6-(2-pyridyl)-2H-5,1-benzothiazocine 5,5-dioxide of melting point 215°–217°.

(e) From 8-bromo-1,3,4,6-tetrahydro-2-oxo-6-(2-pyridyl)-2H-5,1-benzothiazocine 5,5-dioxide there is obtained in analogy to Example 1(e) 7-bromo-1,3-dihydro-5-(2-pyridyl)-2H-1-benzazepin-2-one of melting point 242°.

(f) From 7-bromo-1,3-dihydro-5-(2-pyridyl)-2H-1-benzazepin-2-one there is obtained in analogy to Example 1(f) 7-bromo-1,3-dihydro-5-(2-pyridyl)-2H-1-benzazepine-2-thione of melting point 265°–267°.

(g) From 7-bromo-1,3-dihydro-5-(2-pyridyl)-2H-1-benzazepine-2-thione there is obtained in analogy to Example 1(g) 8-bromo-1-methyl-6-(2-pyridyl)-4H-s-triazolo[4,3-a][1]-benzazepine of melting point 201°–202°.

EXAMPLE 4

(a) From 2-amino-2'-chloro-5-nitrobenzophenone there is obtained in analogy to Example 1(a) 2-amino-2'-chloro-5-nitrobenzhydrol of melting point 127°–128°

(b) From 2-amino-2'-chloro-5-nitrobenzhydrol there is obtained in analogy to Example 1(b) 3-[(2-amino-5-nitrophenyl)(2-chlorophenyl)methylthio]propionic acid hydrochloride of melting point 176°.

(c) By cyclizing 3-[(2-amino-5-nitrophenyl)(2-chlorophenyl)methylthio]propionic acid hydrochloride in analogy to Example 1(c), but in tetrahydrofuran and using ethyl chloroformate and pyridine, there is obtained 6-(2-chlorophenyl)-1,3,4,6-tetrahydro-8-nitro-2H-5,1-benzothiazocin-2-one of melting point 285°.

(d) From 6-(2-chlorophenyl)-1,3,4,6-tetrahydro-8-nitro-2H-5,1-benzothiazocin-2-one there is obtained in analogy to Example 1(d) 6-(2-chlorophenyl)-1,3,4,6-tetrahydro-8-nitro-2-oxo-5,1-benzothiazocine 5,5-dioxide of melting point 280°.

(e) From 6-(2-chlorophenyl)-1,3,4,6-tetrahydro-8-nitro-2-oxo-5,1-benzothiazocine 5,5-dioxide there is obtained in analogy to Example 1(e) 5-(2-chlorophenyl)-1,3-dihydro-7-nitro-2H-1-benzazepin-2-one of melting point 224°–226°.

(f) 2.36 g of 5-(2-chlorophenyl)-1,3-dihydro-7-nitro-2H-1-benzazepin-2-one and 9.2 ml of N,N-dimethylaniline are dissolved in 100 ml of chloroform which has been filtered over aluminium oxide (activity grade I). After adding 2.8 ml of phosphorus oxychloride, the mixture is heated to boiling under reflux for 12 hours. The mixture obtained is poured into a solution of 12 g of sodium hydrogen carbonate in 300 ml of water and stirred at room temperature for 20 minutes. The chloroform solution is separated, washed, dried and evaporated in vacuo. The residue consists of crude 2-chloro-5-(2-chlorophenyl-7-nitro-3H-1-benzazepine and dimethylaniline.

(g) The above residue is dissolved in 150 ml of n-butanol, treated with 11 g of acetic acid hydrazide and heated to boiling under reflux for 1 hour. The solution obtained is evaporated in vacuo. The residue is dissolved in 150 ml of glacial acetic acid and heated to boiling under reflux for 2 hours. After concentration in vacuo, the residue is partitioned between chloroform and saturated sodium hydrogen carbonate solution. The chloroform solution is concentrated in vacuo and the residue is chromatographed on 250 g of silica gel. Impurities are firstly eluted with chloroform/ethanol (99:1 and 98:2). The desired product is eluted with chloroform/ethanol (97:3 and 94:6). The residues from these eluates are crystallized from ethyl acetate/ether and then recrystallized from ethyl acetate. There is obtained 6-(2-chlorophenyl)-1-methyl-8-nitro-4H-s-triazolo[4,3-a][1]benzazepine of melting point 225°–227°.

EXAMPLE 5

(a) 100 g of 2-fluorodiphenylmethane are slowly added dropwise to a solution of sodiuum amide which has been prepared from 500 ml of liquid ammonia, 0.22 g of iron (III) nitrate and 13.2 g of sodium. After 10 minutes, a solution of 40.75 g of 3-bromopropionic acid in 500 ml of ether is added dropwise. After a further 15 minutes, the ammonia is allowed to distill off. The crystallized-out sodium salt of 4-(2-fluorophenyl)-4-phenylbutyric acid is filtered off and washed with ether. The free acid is obtained by treating the sodium salt with dilute hydrochloric acid, extracting the mixture with ether and evaporating the ethereal solution. There is obtained 4-(2-fluorophenyl)-4-phenylbutyric acid of melting point 105°.

(b) 50 g of 4-(2-fluorophenyl)-4-phenylbutyric acid are dissolved in 250 g of polyphosphoric acid and heated to 125° for 40 minutes while stirring. After cooling to room temperature, the mixture is mixed with ice and extracted with chloroform. The chloroform extracts are washed neutral with sodium hydrogen carbonate solution and water and then evaporated. The crude product is chromatographed on 500 g of aluminium oxide (activity grade III). 4-(2-Fluorophenyl)-1-tetralone is obtained by elution with benzene.

(c) 32 g of 4-(2-fluorophenyl)-1-tetralone in 75 ml of ethanol are treated with a solution of 9.26 g of hydroxylamine hydrochloride in 10 ml of water and then with 17 g of powdered sodium hydroxide. The mixture is heated to boiling under reflux for 5 minutes, again cooled and then poured into a mixture of ice and dilute hydrochloric acid. The mixture is extracted with ether and the extract obtained is washed with water. After evaporation of the solvent, there is obtained 4-(2-fluorophenyl)-1-tetralone oxime of melting point 120°.

(d) 26 g of 4-(2-fluorophenyl)-1-tetralone oxime are added to 130 g of polyphosphoric acid pre-heated to 125°. The solution obtained is stirred at 125° for 30 minutes, cooled, mixed with ice and water and extracted with chloroform. After evaporation of the organic phase, the residue is crystallized from ethanol. There is obtained 5-(2-fluorophenyl)-1,3,4,5-tetrahydro-2H-1-benzazepin-2-one of melting point 210°–212°.

(e) A solution of 17.1 g of 5-(2-fluorophenyl)-1,3,4,5-tetrahydro-2H-1-benzazepin-2-one in 135 ml of dimethylformamide is treated with 9.4 g of N-chlorosuccinimide. The mixture is heated to 100° for 1 hour, then cooled and diluted with water. The precipitated product is extracted with ethyl acetate. The solution obtained is concentrated to a small volume, 7-chloro-5-(2-fluorophenyl)-1,3,4,5-tetrahydro-2H-1-benzazepin-2-one of melting point 185° crystallizing out.

(f) A suspension of 10.25 g of 7-chloro-5-(2-fluorophenyl)-1,3,4,5-tetrahydro-2H-1-benzazepin-2-one in 880 ml of carbon tetrachloride is treated with 4.5 ml of bromine and heated to boiling while stirring for 2 hours while irradiating with a 500 W incandescent lamp. The solution is evaporated in vacuo. The residue is dissolved in 880 ml of 2 propanol and hydrogenated at room temperature and normal pressure in the presence of 1.3 g of palladium-on-carbon (5%). The catalyst is filtered off and the filtrate is evaporated. The residue is dissolved in benzene and chromatographed on 295 g of silica gel. Impurities and starting material are eluted with benzene/ethyl acetate (29:1) and the desired product is eluted with benzene/ethyl acetate (19:1). After recrystallization from benzene/ether, there is obtained 7-chloro-5-(2-fluorophenyl)-1,3-dihydro-2H-1-benzazepin-2-one of melting point 214°–215°.

(g) A solution of 4 g of 7-chloro-5-(2-fluorophenyl)-1,3-dihydro-2-1-benzazepin-2-one in 80 ml of methylene chloride is treated with 10.5 g of triethyloxonium tetrafluoroborate and stirred at room temperature for 65 hours. The mixture is subsequently treated with 12.1 ml of a 50 percent potassium carbonate solution. Sodium sulphate is then added and the mixture is stirred for a further 30 minutes. The insoluble constituents are filtered off and washed with methylene chloride. The filtrate is evaporated. The crude 2-ethoxy-7-chloro-5-(2-fluorophenyl)-3H-1-benzazepine obtained is treated with a solution of 3.1 g of acetic acid hydrazide in 60 ml of n-butanol. The mixture is heated to boiling under reflux for 24 hours and then evaporated in vacuo. After partitioning the residue between chloroform and water, the chloroform solution is evaporated in acuo and the residue is recrystallized from ether and then from benzene. There is obtained 8-chloro-6-(2-fluorophenyl)-1-methyl-4H-s-triazolo[4,3-a][1]benzazepine of melting point 223°–225°.

EXAMPLE 6

(a) From 7-chloro-5-(2-fluorophenyl)-1,3-dihydro-2H-1-benzazepin-2-one and (benzyloxycarbonylamino)-acetic acid hydrazide there is obtained in analogy to Example 5(g) benzyl [[8-chloro-6-(2-fluoropheny)-4H-s-triazolo[4,3-a][1]benzazepin-1-yl]methyl]carbamate of melting point 161°–163°.

(b) A solution of 4.5 g of benzyl [[8-chloro-6-(2-fluorophenyl)-4H-s-triazolo[4,3-a][1]benzazepin-1-yl]methyl]carbamate in 23 ml of glacial acetic acid is treated at room temperature with 23 ml of a 2.3 M solution of hydrobromic acid in glacial acetic acid. The mixture is warmed to 40° for 2 hours, cooled to room temperature and diluted with 200 ml of ether. The crystallized-out 1-(aminomethyl)-8-chloro-6-(2-fluorophenyl)-4H-s-triazolo[4,3-a][1]benzazepine hydrobromide is filtered off.

The free base is obtained from the above hydrobromide by treatment with aqueous ammonia and extraction with chloroform. The residue from the chloroform extract is recrystallized from benzene/ether. There is obtained 1-(aminomethyl)-8-chloro-6-(2-fluorophenyl)-4H-s-triazolo[4,3-a][1]benzazepine of melting point 188°–190°.

For conversion into the hydrochloride, the base is dissolved in isopropanol and treated with an equivalent amount of hydrogen chloride in isopropanol. After evaporation of the solvent and recrystallization of the hydrochloride from a ten-fold amount of water, there is obtained 1-(aminomethyl)-8-chloro-6-(2-fluorophenyl)-4H-s-triazolo[4,3-a][1]benzazepine hydrochloride of melting point 246°–248° (decomposition).

EXAMPLE 7

From 7-chloro-1,3-dihydro-5-phenyl-2H-1-benzazepine-2-one and acetic acid hydrazide there is obtained in analogy to Example 5(g), via 2-ethoxy-7-chloro-5-phenyl-3H-1-benzazepine, 8-chloro-1-methyl-6-phenyl-4H-s-triazolo[4,3-a][1]benzazepine of melting point 235°.

EXAMPLE 8

(a) From 7-chloro-5-(2-chlorophenyl)-1,3-dihydro-2-1-benzazepin-2-one and (benzyloxycarbonylamino)-acetic acid hydrazide there is obtained in analogy to Example 5(g), via 2-ethoxy-7-chloro-5-(2-chlorophenyl)-3H-1-benzazepine, benzyl [[8-chloro-6-(2-chlorophenyl)-4H-s-triazolo[4,3-a][1]benzazepin-1-yl]methyl]carbamate of melting point 190°.

(b) From benzyl [[8-chloro-6-(2-chlorophenyl)-4H-s-triazolo[4,3-a][1]benzazepin-1yl]methyl]carbamate there is obtained in analogy to Example 6(b) 1-(aminomethyl)-8-chloro-6-(2-chlorophenyl)-4H-s-triazolo[4,3-a][1]benzazepine of melting point 208°–209° and the corresponding hydrochloride of melting point 256°–258° (decomposition).

EXAMPLE 9

A solution of 1.075 g of 7-chloro-5-phenyl-1,3-dihydro-2H-1-benzazepin-2-one in 20 ml of dry tetrahydrofuran is treated with 0.23 g of sodium hydride (50% dispersion in mineral oil) and stirred at 60° for 1 hour. The mixture is then cooled to room temperature, treated with 1.53 g of bis-(4-morpholinyl)phosphinic acid chloride and stirred at this temperature for a further 2 hours. A solution of 0.593 g of acetic acid hydrazide in 50 ml of n-butanol is subsequently added thereto, the mixture is heated to boiling under reflux for 1 hour and then evaporated in vacuo. The residue is partitioned between water and methylene chloride. The methylene chloride solution is evaporated and the residue is chromatographed on 100 g of aluminium oxide (activity grade III). Various impurities and starting material are eluted successively with benzene and ethyl acetate/hexane (1:1). After elution with chloroform/ethanol (96:4) and recrystallization of the crude product from ethyl acetate/benzene/n-hexane, there is obtained 8-chloro-1-methyl-6-phenyl-4H-s-triazolo[4,3-a][1]benzazepine of melting point 235°.

EXAMPLE 10

(a) 100 g of 2-amino-2'-chloro-5-nitrobenzophenone are suspended in 865 ml of 25% hydrochloric acid and treated portionwise with a total of 269 g of tin (II) chloride. The mixture is stirred at room temperature for 36 hours, then diluted with 0.5 l of an ice/water mixture and adjusted to pH 10 with about 2.17 l of a 28% sodium hydroxide solution. The mixture is extracted with methylene chloride. After evaporation of the solvent, the residue is dissolved in 0.54 l of ether and crystallized at about −20°. There is obtained 2,5-diamino-2'-chlorobenzophenone of melting point 30°–40°.

(b) A solution of 91.3 g of 2,5-diamino-2'-chlorobenzophenone in 900 ml of methylene chloride is cooled to −30° and treated with 51.6 ml of triethylamine. Then, over a period of 90 minutes there is added dropwise a solution of 35.2 ml of acetic anhydride in 720 ml of methylene chloride and the mixture is left to stand at −25° for 3 hours and at room temperature for 16 hours. 1.4 l of water are then added thereto and the mixture is extracted several times with methylene chloride. The organic extracts are concentrated and treated with ether, 5-acetamino-2-amino-2'-chlorobenzophenone of melting point 157° crystallizing out.

(c) A solution of 108.92 g of 5-acetamino-2-amino-2'-chlorobenzophenone in 1.4 l of ethanol is treated dropwise at room temperature with a solution of 15.9 g of sodium borohydride in 100 ml of water. The solution obtained is then heated to boiling under reflux until decolourization occurs and subsequently, after the addition of 300 ml of methanol, heated for a further 15 minutes. The organic solvents are distilled off in vacuo and the residue is suspended in 0.5 l of water. The crystals obtained are recrystallized from ethanol/water. There is obtained 5-acetamino-2-amino-2'-chlorobenzhydrol of melting point 137°–138°.

(d) 107.3 g of 5-acetamino-2-amino-2'-chlorobenzhydrol are heated to 90° for 1 hour together with 36.8 g of 3-mercaptopropionic acid in 290 ml of 6N hydrochloric acid. After cooling, the crystals are filtered off. There is obtained 3-[(2,5-diaminophenyl)(2-chlorophenyl)methylthio]propionic acid dihydrochloride of melting point 234°–235° (decomposition).

(e) A solution of 138.2 g of 3-[(2,5-diaminophenyl)(2-chlorophenyl)methylthio]propionic acid dihydrochloride in 8.6 l of dry methylene chloride is treated at −5° with 94 ml of triethylamine. Subsequently, there are successively added thereto at 0° to 2° 129.1 ml of ethyl chloroformate and 188 ml of triethylamine. The cooling means is then removed and the mixture is stirred for a further 90 minutes. The mixture is evaporated and the residue is chromatographed on 1.44 kg of silica gel. Elution is carried out with chloroform in order to remove impurities and then with chloroform/ethanol (89.5:1.5). There is obtained ethyl 6-(2-chlorophenyl)-1,3,4,6-tetrahydro-2-oxo-2H-5,1-benzothiazocine-8-carbamate of melting point 229°–231°.

(f) 64.2 g of ethyl 6-(2-chlorophenyl)-1,3,4,6-tetrahydro-2-oxo-2H-5,1-benzothiazocine-8-carbamate are dissolved in 3.2 l of chloroform. A solution of 105.3 g of m-chloroperbenzoic acid in 630 ml of chloroform is added dropwise thereto. After evaporation of the solvent, there is obtained 8-(ethoxycarbonylamino)-6-(2-chlorophenyl)-1,3,4,6-tetrahydro-2-oxo-2H-5,1-benzothiazocine 5,5-dioxide of melting point 295°–296°.

(g) 93.1 g of 8-(ethoxycarbonylamino)-6-(2-chlorophenyl)-1,3,4,6-tetrahydro-2-oxo-2H-5,1-benzothiazocine 5,5-dioxide are dissolved at 80° in a mixture of 1.3 l of carbon tetrachloride, 1.3 l of t-butanol and 33.5 ml of water. After cooling to 35°, the mixture is treated rapidly with 212 g of potassium t-butylate (in three portions) while cooling strongly. The temperature thereby rises to 45°–50°. After the reaction has faded away, the cooling bath is removed and the mixture is stirred for a further 30 minutes. The mixture is poured on to ice and extracted several times with chloroform. The organic solvents are evaporated and the residue is chromatographed on 310 g of silica gel. The desired product is eluted with toluene/chloroform (1:3). After recrystallization from ethyl acetate/petroleum ether, there is obtained ethyl 5-(2-chlorophenyl)-2,3-dihydro-2-oxo-1H-1-benzazepine-7-carbamate of melting point 241°.

(h) 13.0 g of ethyl 5-(2-chlorophenyl)-2,3-dihydro-2-oxo-1H-1-benzazepine-7-carbamate are heated to boiling under reflux for 13 hours together with 39 g of potassium methylate in a mixture of in each case 215 ml of methanol, ethanol and water. After evaporation of the organic solvents, the residue is extracted with chloroform. The residue from the chloroform extract is crystallized from ethyl acetate. There is obtained 7-amino-5-(2-chlorophenyl)-1,3-dihydro-2H-1-benzazepin-2-one of melting point 192°.

(i) A solution of 9.2 g of 7-amino-5-(2-chlorophenyl)-1,3-dihydro-2H-1-benzazepin-2-one in 230 ml of methylene chloride is treated at 0° with a solution of 22.3 g of m-chloroperbenzoic acid in 190 ml of methylene chloride. The temperature thereby rises to 10°. The mixture is again cooled to 0°, stirred for 2 minutes and then extracted with aqueous sodium hydrogen carbonate solution. The organic phase is then filtered through basic aluminium oxide and, after testing for freedom from peroxide, evaporated. The residue is taken up in toluene and chromatographed on 110 g of silica gel. With toluene/chloroform (4:1) there is eluted 5-(2-chlorophenyl)-1,3-dihydro-7-nitro-2H-1-benzazepin-2-one which has a melting point of 224°–226° after recrystallization from diethyl ether/diisopropyl ether.

(j) 2.36 g of 5-(2-chlorophenyl)-1,3-dihydro-7-nitro-2H-1-benzazepin-2-one and 9.2 ml of N,N-dimethylaniline are dissolved in 100 ml of chloroform which has been filtered over aluminium oxide (activity grade I). After adding 2.8 ml of phosphorus oxychloride, the mixture is heated to boiling under reflux for 12 hours. The mixture obtained is poured into a solution of·12 g of sodium hydrogen carbonate in 300 ml of water and stirred at room temperature for 20 minutes. The chloroform solution is separated, washed, dried and evaporated in vacuo. The residue consists of crude 2-chlor-5-(2-chlorophenyl)-7-nitro-3H-1-benzazepine and dimethylaniline.

(k) The above residue is dissolved in 150 ml of n-butanol, treated with 11 g of acetic acid hydrazide and heated to boiling under reflux for 1 hour. The solution obtained is evaporated in vacuo. The residue is dissolved in 150 ml of glacial acetic acid and heated to boiling under reflux for 2 hours. After concentration in vacuo, the residue is partitioned between chloroform and saturated sodium hydrogen carbonate solution. The chloroform solution is concentrated in vacuo and the residue is chromatographed on 250 g of silica gel. Impurities are firstly eluted with chloroform/ethanol (99:1 and 98:2). The desired product is eluted with chloroform/ethanol (97:3 and 94:6). The residues from these eluates are crystallized from ethyl acetate/ether and then recrystallized from ethyl acetate. There is obtained 6-(2-chlorophenyl)-1-methyl-8-nitro-4H-s-triazolo[4,3-a][1]benzazepine of melting point 225°–227°.

EXAMPLE 11

(a) From 2-chloro-5-(2-chlorophenyl)-7-nitro-3H-1-benzazepine and (benzyloxycarbonylamino) acetic acid hydrazide there is obtained in analogy to Example 10(k) benzyl [[6-(2-chlorophenyl)-8-nitro-4H-s-triazolo[4,3-a][1]benzazepin-1-yl]methyl]carbamate of melting point 194°–195°.

(b) From benzyl [[6-(2-chlorophenyl)-8-nitro-s-triazolo[4,3-a][1]benzazepin-1-yl]methyl]carbamate there is obtained in analogy to Example 6(b) 1-(aminomethyl)-6-(2-chlorophenyl)-8-nitro-4H-s-triazolo[4,3-a][1]benzazepine of melting point 206°–208°, the corresponding hydrobromide of melting point 202°–204° (decomposition) and the corresponding hydrochloride of melting point 262°–263° (decomposition).

EXAMPLE 12

6 g of 7-chloro-5-(2-fluorophenyl)-1,3-dihydro-2H-1-benzazepine-2-thione and 27 g of isonicotinic acid hydrazide are dissolved together in 360 ml of n-butanol and heated to boiling under reflux for 24 hours. After evaporation of the resulting solution in vacuo, the residue is partitioned between toluene and water. The toluene phase is concentrated to about 100 ml. The precipitated crystals are filtered off and recrystallized from benzene. There is obtained 8-chloro-6-(2-fluorophenyl)-1-(4-pyridyl)-4H-s-triazolo[4,3-a][1]benzazepine of melting point 198°–200°.

EXAMPLE 13

From 8 bromo-1,3-dihydro-5-(2-pyridyl)-2H-1-benzazepine-2-thione and isonicotinic acid hydrazide there is obtained in analogy to Example 12 8-bromo-6-(2-pyridyl)-1-(4-pyridyl)-4H-s-triazolo[4,3-a][1]benzazepine of melting point 267°–269°.

EXAMPLE 14

From 7-chloro-5-(2-fluorophenyl)-1,3-dihydro-2H-1-benzazepine-2-thione and dimethylaminoacetic acid hydrazide there is obtained in analogy to Example 12 8-chloro-6-(2-fluorophenyl)-1-(dimethylaminomethyl)-4H-s-triazolo[4,3-a][1]benzazepine of melting point 196°–197°.

EXAMPLE 15

(a) From 8-bromo-1,3-dihydro-5-(2-pyridyl)-2H-1-benzazepine-2-thione and (benzyloxycarbonylamino)acetic acid hydrazide there is obtained in analogy to Example 12 benzyl [[8-bromo-6-(2-pyridyl)-4H-s-triazolo[4,3-a][1]benzazepin-1-yl]methyl]carbamate of melting point 128°–132°.

(b) From benzyl [[8-bromo-6-(2-pyridyl)-4H-s-triazolo[4,3-a][1]benzazepin-1-yl]methyl]carbamate there is obtained in analogy to Example 6(b) 1-(aminomethyl)-8-bromo-6-(2-pyridyl)-4H-s-triazolo[4,3-a][1]benzazepine of melting point 118°–130° and the corresponding maleate of melting point 165° (decomposition).

EXAMPLE 16

(a) A solution of 10 ml of hydrazine hydrate in 1 l of tetrahydrofuran is treated with 12.5 g of 7-chloro-5-(2-fluorophenyl)-1,3-dihydro-2H-1-benzazepine-2-thione and stirred at room temperature for 2 hours under a stream of nitrogen. The mixture is evaporated in vacuo. The residue is crystallized from diisopropyl ether/hexane, 7-chloro-5-(2-fluorophenyl)-2-hydrazino-3H-1-benzazepine of melting point 239°–240° being obtained.

(b) 12.1 g of 7-chloro-5-(2-fluorophenyl)-2-hydrazino-3H-1-benzazepine are heated to boiling under reflux for 2 hours in a mixture of 330 ml of n-butanol and 110 ml of triethyl orthoformate. The mixture is evaporated in vacuo. The residue is crystallized from hexane, there being obtained crude 8-chloro-6-(2-fluorophenyl)-4H-s-triazolo[4,3-a][1]benzazepine as reddish coloured crystals. This material is purified by chromatography on 121 g of silica gel. Impurities are eluted with benzene/methanol (99:1). The product is subsequently eluted with benzene/methanol (98.5:1.5 and 98:2). After crystallization of the resulting material from ether, there is obtained 8-chloro-6-(2-fluorophenyl)-4H-s-triazolo[4,3-a][1]benzazepine of melting point 180°–182°.

EXAMPLE 17

(a) In analogy to Example 16(a), from 7-chloro-5-(2-chlorophenyl)-1,3-dihydro-2H-1-benzazepine-2-thione and hydrazine hydrate there is obtained 7-chloro-5-(2-chlorophenyl)-2-hydrazino-3H-1-benzazepine of melting point 223°–225°.

(b) In analogy to Example 16(b), by reacting 7-chloro-5-(2-chlorophenyl)-2-hydrazino-3H-1-benzazepine with triethyl orthoformate there is obtained 8-chloro-6-(2-chlorophenyl)-4H-s-triazolo[4,3-a][1]benzazepine of melting point 189°–190°.

EXAMPLE 18

(a) In analogy to Example 16(a), from 7-bromo-1,3-dihydro-5-(2-pyridyl)-2H-1-benzazepine-2-thione and hydrazine hydrate there is obtained 7-bromo-2-hydrazino-5-(2-pyridyl)-3H-1-benzazepine of melting point 149° (decomposition).

(b) In analogy to Example 16(b), by reacting 7-bromo-2-hydrazino-5-(2-pyridyl)-3H-1-benzazepine with triethyl orthoformate there is obtained 8-bromo-6-(2-pyridyl)-4H-s-triazolo[4,3-a][1]benzazepine of melting point 219°.

EXAMPLE 19

From 7-chloro-5-(2-fluorophenyl)-2-hydrazino-3H-1-benzazepine and triethyl orthopropionate there is obtained in analogy to Example 16(b) 1-ethyl-8-chloro-6-(2-fluorophenyl)-4H-s-triazolo[4,3-a][1]benzazepine of melting point 238°–239°.

EXAMPLE 20

(a) 8.5 g of 8-chloro-6-(2-fluorophenyl)-4H-s-triazolo[4,3-a][1]benzazepine are dissolved in 135 ml of chloroform and 3.3 ml of pyridine. 2.0 ml of bromine are added dropwise at room temperature while stirring. The mixture is then heated to 55°–60° for 50 minutes and evaporated in vacuo. The residue is chromatographed on 550 g of silica gel. By elution with chloroform which contains 0.3% or 0.4% methanol and crystallization of the obtained material from benzene there is obtained 1-bromo-8-chloro-6-(2-fluorophenyl)-4H-s-triazolo[4,3-a][1]benzazepine of melting point 222°.

(b) 3.9 g of 1-bromo-8-chloro-6-(2-fluorophenyl)-4H-s-triazolo[4,3-a][1]benzazepine are suspended in 90 ml of methanol and treated with 1.62 of g of sodium methylate. The mixture is heated to boiling under reflux for 20 hours and then evaporated. The residue, which contains predominantly 8-chloro-6-(2-fluorophenyl)-1-methoxy-4H-s-triazolo[4,3-a][1]benzazepine, is heated to boiling under reflux for 4.5 hours in 100 ml of 48% hydrobromic acid. The mixture is diluted with water, made weakly alkaline with sodium carbonate and extracted with methylene chloride. The methylene chloride solution is evaporated and the residue is chromatographed on 120 g of aluminium oxide (activity grade III). Impurities are separated by elution with benzene/chloroform (9:1 to 1:4). By elution with chloroform which contains 1% to 10% methanol and two-fold recrystallization of the resulting material from benzene there is obtained 8-chloro-6-(2-fluorophenyl)-2,4-dihydro-1H-s-triazolo[4,3-a][1]benzazepin-1-one of melting point 223°–225°.

EXAMPLE 21

(a) 8.1 g of 8-chloro-6-(2-chlorophenyl)-4H-s-triazolo[4,3-a][1]benzazepine are brominated according to the process described in Example 20(a). There is obtained 1-bromo-8-chloro-6-(2-chlorophenyl)-4H-s-triazolo[4,3-a][1]benzazepine of melting point 234°.

(b) 9 g of 1-bromo-8-chloro-6-(2-chlorophenyl)-4H-s-triazolo[4,3-a][1]benzazepine are stirred at 140° for 22 hours in 263 ml of 85% phosphoric acid. The mixture is poured on to 1.5 kg of ice water and neutralized with 28% sodium hydroxide solution. The product is extracted with chloroform. The residue from the chloroform extracts is chromatographed on 300 g of silica gel. Impurities are separated by elution with chloroform. By elution with chloroform which contains 2% or 4% ethanol, crystallization of the resulting material from diethyl ether/diisopropyl ether and recrystallization from ethyl acetate there is obtained 8-chloro-6-(2-chlorophenyl)-2,4-dihydro-1H-s-triazolo[4,3-a][1]benzazepin-1-one of melting point 250°–251°.

EXAMPLE 22

From 1-bromo-8-chloro-6-(2-fluorophenyl)-4H-s-triazolo[4,3-a][1]benzazepine there is obtained in analogy to Example 21(b) 8-chloro-6-(2-fluorophenyl)-2,4-dihydro-1H-s-triazolo[4,3-a][1]benzazepin-1-one of melting point 223°–225°.

EXAMPLE 23

0.15 g of 7-chloro-5-(2-fluorophenyl)-2-hydrazino-3H-1-benzazepine is dissolved in 10 ml of pyridine and treated with 1.44 ml of a 14.3% solution of phosgene in toluene. The mixture is heated to 60° for 5 minutes and then evaporated in vacuo. The residue is partitioned between benzene and water. The benzene phase is washed successively with water, with sodium hydrogen carbonate solution and with water. The solvent is evaporated in vacuo. The residue is chromatographed on 15 g of silica gel while eluting with benzene/ethyl acetate (19:1 and 9:1). After recrystallization from ether/hexane, there is obtained pure 8-chloro-6-(2-fluorophenyl)-2,4-dihydro-1H-s-triazolo[4,3-a][1]benzazepin-1-one of melting point 223°–225°.

EXAMPLE 24

3 g of 7-chloro-5-(2-fluorophenyl)-2-hydrazino-3H-1-benzazepine are dissolved in 40 ml of dimethylformamide. After adding 3.6 g of N,N'-carbonyldiimidazole, the mixture is stirred at 50° for 16 hours. The solution obtained is then poured into 700 ml of water and extracted with ethyl acetate. The organic extracts are washed with water and saturated sodium chloride solution, dried and evaporated. The residue is chromatographed on 200 g of silica gel while eluting with chloroform/ethanol (98.5:1.5). After recrystallization from diisopropyl ether, there is obtained 8-chloro-6-(2-fluorophenyl)-2,4-dihydro-1H-s-triazolo[4,3-a][1]benzazepin -1-one of melting point 223°–225°.

EXAMPLE 25

A solution of 2.65 g of 8-chloro-6-(2-fluorophenyl)-2,4-dihydro-1H-s-triazolo[4,3-a][1]benzazepin-1-one in a mixture of 16 ml of methanol and 16 ml of methylene chloride is treated at 0° with 100 ml of ethereal diazomethane solution. After 3 hours, a further 33 ml of diazomethane solution are added and the mixture is left to stand for a further 2 hours. After evaporation of the solution, the residue is chromatographed on 80 g of silica gel while eluting with chloroform/ethanol (99:1). The crude product is recrystallized from ether/hexane. There is obtained 8-chloro-6-(2-fluorophenyl)-2,4-dihydro-2-methyl-1H-s-triazolo[4,3-a][1]benzazepin-1-one of melting point 142°–143°.

EXAMPLE 26

5 g of 1-bromo-8-chloro-6-(2-fluorophenyl)-4H-s-triazolo[4,3-a][1]benzazepine are heated to 120° in 40 ml of N-methylpiperazine for 21 hours while stirring. After cooling, the mixture is poured into ice/water and extracted with chloroform. The residue from the chloroform extracts is chromatographed on 150 g of silica gel. After separating impurities by elution with chloroform/ethanol (94:6), the desired product is obtained by elution with chloroform/ethanol (85:15). After recrystallization from diethyl ether/diisopropyl ether and from ethyl acetate/diisopropyl ether, there is obtained 8-chloro-6-(2-fluorophenyl)-1-(4-methyl-1-piperazinyl)-4H-s-triazolo[4,3-a][1]benzazepine of melting point 209°–210°.

EXAMPLE 27

From 1-bromo-8-chloro-6-(2-fluorophenyl)-4H-s-triazolo[4,3-a][1]benzazepine and morpholine there is obtained in analogy to Example 26 8-chloro-6-(2-fluorophenyl)-1-morpholino-4H-s-triazolo[4,3-a][1]benzazepine of melting point 246°–247°.

EXAMPLE 28

From 1-bromo-8-chloro-6-(2-fluorophenyl)-4H-s-triazolo[4,3-a][1]benzazepine and dimethylamine there is obtained in analogy to Example 26, but using a bomb-tube and heating to 120° for 2 hours and to 150° after 2 hours, 1-dimethylamino-8-chloro-6-(2-fluorophenyl)-4H-s-triazolo[4,3-a][1]benzazepine of melting point 240°–243°.

EXAMPLE 29

(a) A solution of 18.2 g of 7-chloro-5-(2-fluorophenyl)-2-hydrazino-3H-1-benzazepine in 220 ml of glacial acetic acid is treated dropwise at 15° with 5.1 ml of chloroacetyl chloride. The mixture is stirred at room temperature for a further 2 hours. The mixture is treated with 7.5 g of sodium acetate, stirred at room temperature for 2 hours. and at boiling under reflux for 20 minutes, then evaporated in vacuo and the residue is partitioned between chloroform and water. The organic phase is washed with sodium hydrogen carbonate solution and water and evaporated. The crude product obtained is chromatographed on silica gel while eluting with chloroform/ethanol (98.5:1.5) and there is obtained 8-chloro-1-(chloromethyl)-6-(2-fluorophenyl)-4H-s-triazolo[4,3-a][1]benzazepine as white crystals of melting point 180° (decomposition).

(b) 7 g of 8-chloro-1-(chloromethyl)-6-(2-fluorophenyl)-4H-s-triazolo[4,3-a][1]benzazepine and 2.9 g of sodium iodide are dissolved in 195 ml of acetone. The solution is stirred at room temperature for 2 hours, the precipitated sodium chloride is filtered off and the filtrate is treated with methylamine while stirring until the reaction remains basic. After a further 10 minutes, the mixture is evaporated. The residue is partitioned between ethyl acetate and dilute hydrochloric acid. The aqueous solutions are made alkaline with ammonia, saturated with sodium chloride and extracted with chloroform. The chloroform extracts are evaporated. The residue is chromatographed on 300 g of silica gel while eluting with chloroform/ethanol (9:1). After recrystallization from ethyl acetate/diisopropyl ether, there is obtained 8-chloro-6-(2-fluorophenyl)-1-(methylaminomethyl)-4H-s-triazolo[4,3-a][1]benzazepine of melting point 170°–171°.

For conversion into the hydrochloride, this substance is dissolved in ethanol and treated with the calculated amount of hydrogen chloride in ethyl acetate. After adding ether, 8-chloro-6-(2-fluorophenyl)-1-(methylaminomethyl)-4H-s-triazolo[4,3-a][1]benzazepine hydrochloride of melting point 240° (decomposition) crystallizes out.

EXAMPLE 30

From 8-chloro-1-(chloromethyl)-6-(2-fluorophenyl)-4H-s-triazolo[4,3-a][1]benzazepine and N-methyl-N-propargylamine there is obtained in analogy to Example 29(b) 8-chloro-6-(2-fluorophenyl)-1-(N-methyl-N-propargylaminomethyl)-4H-s-triazolo[4,3-a][1]benzazepine of melting point 147° and the corresponding hydrochloride of melting point 204° (decomposition).

EXAMPLE 31

(a) A solution of 13.4 g of 8-chloro-6-(2-fluorophenyl)-1,3,4,6-tetrahydro-2-oxo-2H-5,1-benzothiazocine 5,5-dioxide in 380 ml of hexamethylphosphoric acid triamide is treated with 7.7 g of 2,4-bis-(4-methoxyphenyl)-1,2,3,4-dithiadiphosphetane-2,4-disulphide, the mixture is heated to 100° for 2 hours, again cooled to room temperature and then poured into 8.3 l of water. The mixture is extracted twice with ethyl acetate and the organic extracts are washed with water and with saturated sodium chloride solution. The ethyl acetate solutions are evaporated and the residue is chromatographed on 500 g of silica gel. By elution with chloroform which contains 0.5% ethanol and crystallization from ether there is obtained 8-chloro-6-(2-fluorophenyl)-1,3,4,6-tetrahydro-2-thiono-2H-5,1-benzothiazocine 5,5-dioxide of melting point 226°.

(b) A solution of 0.9 ml of hydrazine hydrate in 134 ml of tetrahydrofuran is treated with 6.2 g of 8-chloro-6-(2-fluorophenyl)-1,3,4,6-tetrahydro-2-thiono-2H-5,1-benzothiazocine 5,5-dioxide. The solution is stirred at room temperature under a stream of argon for 1.25 hours and then evaporated in vacuo. The residue is crystallized from diisopropyl ether, there being obtained 8-chloro-6-(2-fluorophenyl)-2-hydrazino-3,6-dihydro-4H-5,1-benzothiazocine 5,5-dioxide of melting point 159°.

(c) 5.8 g of N,N'-carbonyldiimidazole are added to a solution of 5.9 g of 8-chloro-6-(2-fluorophenyl)-2-hydrazino-3,6-dihydro-4H-5,1-benzothiazocine 5,5-dioxide in 118 ml of dimethylformamide and the mixture is stirred at 52° for 18 hours. The solution obtained is then poured into 1.8 l of water and extracted three times with 1.2 l of ethyl acetate. The organic extracts are washed with water and saturated sodium chloride solution, dried and evaporated. The residue is crystallized from chloroform and recrystallized from ethyl acetate. There is obtained 9-chloro-7-(2-fluorophenyl)-4,5-dihydro-7H-s-triazolo[3,4-a][1]-benzothiazocin-1(2H)-one 6,6-dioxide of melting point 292°-293°.

(d) 591 mg of 9-chloro-7-(2-fluorophenyl)-4,5-dihydro-7H-s-triazolo[3,4-a][1]benzothiazocin-1(2H)-one 6,6-dioxide are suspended in a mixture of 6.0 ml of carbon tetrachloride, 6.0 ml of t-butanol and 0.34 ml of water and cooled to 10°. The mixture is treated with 1.5 g of potassium t-butylate while stirring intensively, the temperature being held at 30° with an ice-bath. The mixture is stirred at 20° for a further 30 miinutes, poured into water and extracted five times with chloroform. The extracts are washed with water and saturated sodium chloride solution, dried and evaporated. The residue is chromatographed on 20 g of silica gel. By elution with chloroform which contains 2% ethanol and crystallization from ether there is obtained 8-chloro-6-(2-fluorophenyl)-2,4-dihydro-1H-s-triazolo[4,3-a][1]benzazepin-1-one of melting point 222°-224.

EXAMPLE 32

(a) 500 mg of 8-chloro-1-(chloromethyl)-6-(2-fluorophenyl)-4H-s-triazolo[4,3-a][1]benzazepine and 212 mg of sodium iodide are dissolved in 14 ml of acetone. The mixture is stirred at room temperature for 1 hour and then the precipitated sodium chloride is filtered off. The filtrate is evaporated at 40° C. in vacuo. The residue, which mainly consists of 8-chloro-1-(iodomethyl)-6-(2-fluorophenyl)-4H-s-triazolo[4,3-a][1]benzazepine, and 308 mg of potassium phthalimide are dissolved in 15 ml of tetrahydrofuran. The solution is stirred at room temperature for 3.5 days, then poured into water and extracted twice with ethyl acetate. The organic extracts are washed with water, dried and evaporated. The residue is chromatographed on 30 g of silica gel while eluting with ethyl acetate/ethanol (9:1) and subsequently crystallized from ethyl acetate/ether. There is obtained 8-chloro-1-(phthalimidomethyl)-6-(2-fluorophenyl)-4H-s-triazolo[4,3-a][1]benzazepine of melting point 235°-237°.

(b) 235 mg of 8-chloro-1-(phthalimidomethyl)-6-(2-fluorophenyl)-4H-s-triazolo[4,3-a][1]benzazepine are dissolved in 15 ml of ethanol and treated with 500 ml of hydrazine hydrate. The mixture is stirred at room temperature for 2 hours and then the ethanol is evaporated in vacuo. The residue is dissolved in ethyl acetate, washed twice with water, dried and evaporated. The residue is chromatographed on 10 g of aluminium oxide (neutral, activity grade III). By elution with chloroform/ethanol (9:1) and crystallization from ethyl acetate there is obtained 1-(aminomethyl)-8-chloro-6-(2-fluorophenyl)-4H-s-triazolo[4,3-a][1]benzazepine of melting point 187°-190°.

EXAMPLE 33

(a) 1.08 g of 8-chloro-1-(chloromethyl)-6-(2-fluorophenyl)-4H-s-triazolo[4,3-a][1]benzazepine and 458 mg of sodium iodide are dissolved in 30 ml of acetone. The mixture is stirred at room temperature for 1 hour, the precipitated sodium chloride is filtered off and the filtrate is evaporated at 40° in vacuo. The residue, which consists mainly of 8-chloro-1-(iodomethyl)-6-(2-fluorophenyl)-4H-s-triazolo[4,3-a][1]benzazepine, and 198 mg of sodium azide are dissolved in 30 ml of tetrahydrofuran. The solution is stirred at room temperature for 18 hours and then evaporated in vacuo. The residue is dissolved in chloroform and washed twice with water. The organic phase is dried, filtered and then evaporated in vacuo. The residue obtained is chromatographed on 20 g of silica gel while eluting with ethyl acetate and yields, after crystallization from isopropyl ether, 1-(azidomethyl)-8-chloro-6-(2-fluorophenyl)-4H-s-triazolo[4,3-a][1]benzazepine of melting point 147°-150°.

(b) 734 mg of 1-(azidomethyl)-8-chloro-6-(2-fluorophenyl)-4H-s-triazolo[4,3-a][1]benzazepine are dissolved in ethanol and cooled to 0°. At this temperature there is added dropwise a solution of 675 mg of tin (II) chloride dihydrate in 9.5 ml of 2N sodium hydroxide. The mixture is stirred at 0°-5° for 45 minutes, then diluted with ethyl acetate and washed four times with water. The organic phase is dried and evaporated. By crystallization from ethyl acetate there is obtained 1-(aminomethyl)-8-chloro-6-(2-fluorophenyl)-4H-s-triazolo[4,3-a][1]benzaepine of melting point 187°-190°.

EXAMPLE 34

(a) 30 g of 7-chloro-5-(2-fluorophenyl)-1,3,4,5-tetrahydro-2H-1-benzazepin-2-one are dissolved in 105 ml of hexamethylphosphoric acid triamide and treated with 22 g of 2,4-bis-(4-methoxyphenyl)-1,2,3,4-dithiadiphosphetane-2,4-disulphide. The mixture is heated to 100° for 1 hour, again cooled to room temperature and poured into 1.41 l of water. The mixture is extracted four times with ethyl acetate and the organic extracts are washed with water. The ethyl acetate solution is dried, filtered and evaporated in vacuo. After crystallization of the residue from ethanol, there is obtained 7-chloro-5-(2-fluorophenyl)-1,3,4,5-tetrahydro-2H-1-benzazepine-2-thione of melting point 190°.

(b) A solution of 17.5 ml of hydrazine hydrate in 1.75 l of tetrahydrofuran is treated with 22 g of 7-chloro-5-(2-fluorophenyl)-1,3,4,5-tetrahydro-2H-1-benzazepine- 2-thione. The solution is stirred under a stream of argon for 2 hours and then evaporated at 40° in vacuo. The residue is crystallized from ether and there is obtained 7-chloro-5-(2-fluorophenyl)-2-hydrazino-4,5-dihydro-2H-1-benzazepine of melting point 213°–215°.

(c) 15.0 g of 7-chloro-5-(2-fluorophenyl)-2-hydrazino-4,5-dihydro-2H-1-benzazepine are dissolved in 200 ml of dimethylformamide. After adding 18 g of N,N'-carbonyl-diimidazole, the mixture is stirred at 52° for 20 hours, poured into 2 l of water and extracted with ethyl acetate. The organic extracts are washed with water, dried and evaporated. The residue is chromatographed on 800 g of silica gel. By elution with chloroform which contains 2% ethanol and crystallization from ether there is obtained 8-chloro-6-(2-fluorophenyl)-2,4,5,6-tetrahydro-1H-s-triazolo[4,3-a][1]benzazepin-1-one of melting point 236°–238°.

(d) A suspension of 660 mg of 8-chloro-6-(2-fluorophenyl)-2,4,5,6-tetrahydro-1H-s-triazolo[4,3-a][1]benzazepin-1-one in 150 ml of carbon tetrachloride is treated with 0.11 ml of bromine and heated to boiling while stirring for 2 hours while irradiating with a 500 W incandescent lamp. The solution is evaporated in vacuo. The residue is dissolved in chloroform and the solution is washed twice with saturated sodium hydrogen carbonate solution, dried and evaporated in vacuo. The residue is chromatographed on 35 g of silica gel. By elution with toluene/ethyl acetate (4:1) and crystallization from ethyl acetate/ether there is obtained 8-chloro-6-(2-fluorophenyl)-2,4-dihydro-1H-s-triazolo[4,3-a][1]benzazepin-1-one of melting point 221°–224°.

EXAMPLE 35

(a) A suspension of 195 mg of 6-(2-chlorophenyl)-1-methyl-8-nitro-4H-s-triazolo[4,3-a][1]benzazepine in 5 ml of concentrated hydrochloric acid is treated with 375 mg of tin (II) chloride, whereupon the mixture is heated to 50° for 40 hours while stirring. After cooling to room temperature, the mixture is neutralized with sodium hydrogen carbonate solution and extracted with chloroform. The chloroform extracts are dried and then evaporated. The residue is crystallized from ethyl acetate/ether, there being obtained 8-amino-6-(2-chlorophenyl)-1-methyl-4H-s-triazolo[4,3-a][1]benzazepine of melting point 271°–273°.

(b) A solution of 155 mg of 8-amino-6-(2-chlorophenyl)-1-methyl-4H-s-triazolo[4,3-a][1]benzazepine in 1 ml of 2N methanesulphonic acid is cooled to 0° and treated with a solution of 44 mg of sodium nitrite in 0.2 ml of water. The mixture is stirred at 5° for 5 minutes and then added to a solution of 206 mg of copper (I) bromide in 2.4 ml of 48% hydrobromic acid. The mixture is stirred at room temperature for a further 10 minutes, whereupon it is neutralized with sodium hydrogen carbonate solution and extracted with chloroform. The chloroform extracts are dried and then evaporated. The residue is dissolved in chloroform and chromatographed on 5 g of silica gel. Impurities are eluted with chloroform and the desired product is eluted with chloroform/ethanol (19:1). After crystallization from ethyl acetate/ether, there is obtained 8-bromo-6-(2-chlorophenyl)-1-methyl-4H-s-triazolo[4,3-a][1]benzazepine of melting point 250°–252°.

EXAMPLE A

Manufacture of tablets of the following composition:

|  | mg/tablet |
|---|---|
| 8-Chloro-6-(2-fluorophenyl)-2,4-dihydro-1H—s-triazolo[4,3-a][1]benzazepin-1-one | 15 |
| Lactose | 110 |
| Maize starch | 61 |
| Talc | 3.4 |
| Magnesium stearate | 0.5 |
| Tablet weight | 190.0 |

The ingredients are mixed with one another and pressed to tablets each weighing 190 mg. The tablets are subsequently coated with ethylcellulose and Carbowax.

The following active substances provided by the invention can be incorporated into the tablets in place of 8-chloro-6-(2-fluorophenyl)-2,4-dihydro-1H-s-triazolo[4,3-a][1]benzazepin-1-one:

8-chloro-6-(2-fluorophenyl)-1-methyl-4H-s-triazolo[4,3-a][1]benzazepine, 8-chloro-6-(2-chlorophenyl)-1-methyl-4H-s-triazolo[4,3-a][1]benzazepine, 8-chloro-6-(2-fluorophenyl)-4H-s-triazolo[4,3-a][1]benzazepine and 1-(aminoethyl)-8-chloro-6-(2-fluorophenyl)-4H-s-triazolo[4,3-a][1]benzazepine.

EXAMPLE B

Manufacture of ampoules:

5.0 g of 1-(aminomethyl)-8-chloro-6-(2-fluorophenyl)-4H-s-triazolo[4,3-a][1]benzazepine hydrochloride and 8.5 g of sodium chloride are dissolved in 900 ml of doubly-distilled water while warming slightly. The solution is subsequently treated with 0.1 N hydrochloric acid until a pH of 4.0–3.0 is reached and then with doubly-distilled water up to a total volume of 1000 ml. The solution is filled into ampoules of 2 ml to 10 ml. After sealing the ampoules, they are sterilized in the usual manner by heating in an autoclave.

What is claimed:

1. A compound of the formula

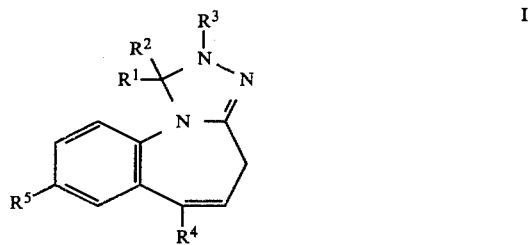

wherein either $R^1$ is hydrogen, lower alkyl, 4-pyridyl or the group —(CH$_2$)$_n$—NR$^6$R$^7$ and $R^2$ and $R^3$ together are an additional bond or $R^1$ and $R^2$ together are the oxo group and $R^3$ is hydrogen or lower alkyl, $R^4$ is phenyl, 0-halophenyl or 2-pyridyl, $R^5$ is halogen or nitro and either $R^6$ is hydrogen or lower alkyl and $R^7$ is hydrogen, lower alkyl, lower alkenyl or lower alkynyl or $R^6$ and $R^7$ together with the nitrogen aton are 4-(lower alkyl)-1-piperazinyl or 4-morpholinyl and n is the number 0 or 1, and pharmaceutically acceptable acid addition salts thereof.

2. The compound of claim 1, wherein $R^1$ is hydrogen, methyl or aminomethyl and $R^2$ and $R^3$ together are an additional bond or $R^1$ and $R^2$ together are the oxo group and $R^3$ is hydrogen.

3. The compound of claim 2, wherein $R^4$ is 0-chlorophenyl or 0-fluorophenyl.

4. The compound of claim 3, wherein $R^5$ is chlorine.

5. The compound: 8-Chloro-6-(2-fluorophenyl)-2,4-dihydro-1H-s-triazolo[4,3-a][1]benzazepin-2-one.

6. The compound: 1-(Aminomethyl)-8-chloro-6-(2-fluorophenyl)-4H-s-triazolo[4,3-a][1]benzazepine.

7. The compound: 8-Chloro-6-(2-fluorophenyl)-1-methyl-4H-s-triazolo-[4,3-a][1]benzazepine.

8. A compound of the formula

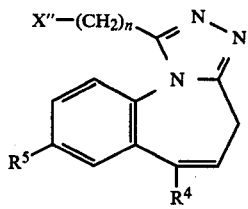

V wherein $R^4$ is phenyl, 0-halophenyl or 2-pyridyl, $R^5$ is halogen or nitro, n is the number 0 or 1 and X'' is a leaving group.

9. A compound of the formula

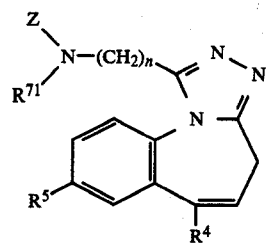

VII wherein $R^4$ is phenyl, 0-halophenyl or 2-pyridyl, $R^5$ is halogen or nitro, n is the number 0 or 1 and either Z is a protecting group and $R^{71}$ is hydrogen, lower alkyl, lower alkenyl or lower alkynyl or Z and $R^{71}$ together are a protecting group.

* * * * *